United States Patent [19]

Gregg, II et al.

[11] Patent Number: 5,642,997
[45] Date of Patent: Jul. 1, 1997

US005642997A

[54] LASER EXCISIONAL NEW ATTACHMENT PROCEDURE

[76] Inventors: Robert H. Gregg, II, 10929 South St., #106-B, Cerritos, Calif. 90703; Delwin K. McCarthy, P.O. Box 3054, Hemet, Calif. 92546

[21] Appl. No.: 595,310

[22] Filed: Feb. 1, 1996

[51] Int. Cl.$^6$ .................................................. A61C 3/00
[52] U.S. Cl. ....................................................... 433/215
[58] Field of Search ............................ 433/29, 215, 216; 606/13, 14, 15; 607/88, 92

[56] References Cited

U.S. PATENT DOCUMENTS

| | | | |
|---|---|---|---|
| 4,764,114 | 8/1988 | Jeffcoat et al. | 433/72 |
| 5,090,908 | 2/1992 | Teumim-Stone | 433/215 |
| 5,194,005 | 3/1993 | Levy | 433/215 |
| 5,230,621 | 7/1993 | Jacoby | 433/29 |
| 5,300,067 | 4/1994 | Nakajima et al. | 606/16 |
| 5,328,365 | 7/1994 | Jacoby | 433/29 |

*Primary Examiner*—Nicholas D. Lucchesi
*Attorney, Agent, or Firm*—Gene Scott

[57] ABSTRACT

A method for removing deep gingival pockets provides for excise of disease while providing for reconnection of the tissue-tooth connection. Steps in the process include creating a gingival trough in the pocket with a contact laser fiber, excising the pocket epithelium while selectively removing sulcular and pocket epithelium and granulation tissue fully around the targeted tooth to the full depth without breaking through the mucogingival junction, scaling the root surfaces to the full depth ultrasonically, lasing the pocket to remove granulation tissue and to disinfect the tissue, assist in hemostatis, cauterize free nerve endings, seal lymphatics, prepare the tissue for welding and desensitize the tooth, and compressing the tissue against the tooth until adhesion is achieved.

10 Claims, 1 Drawing Sheet

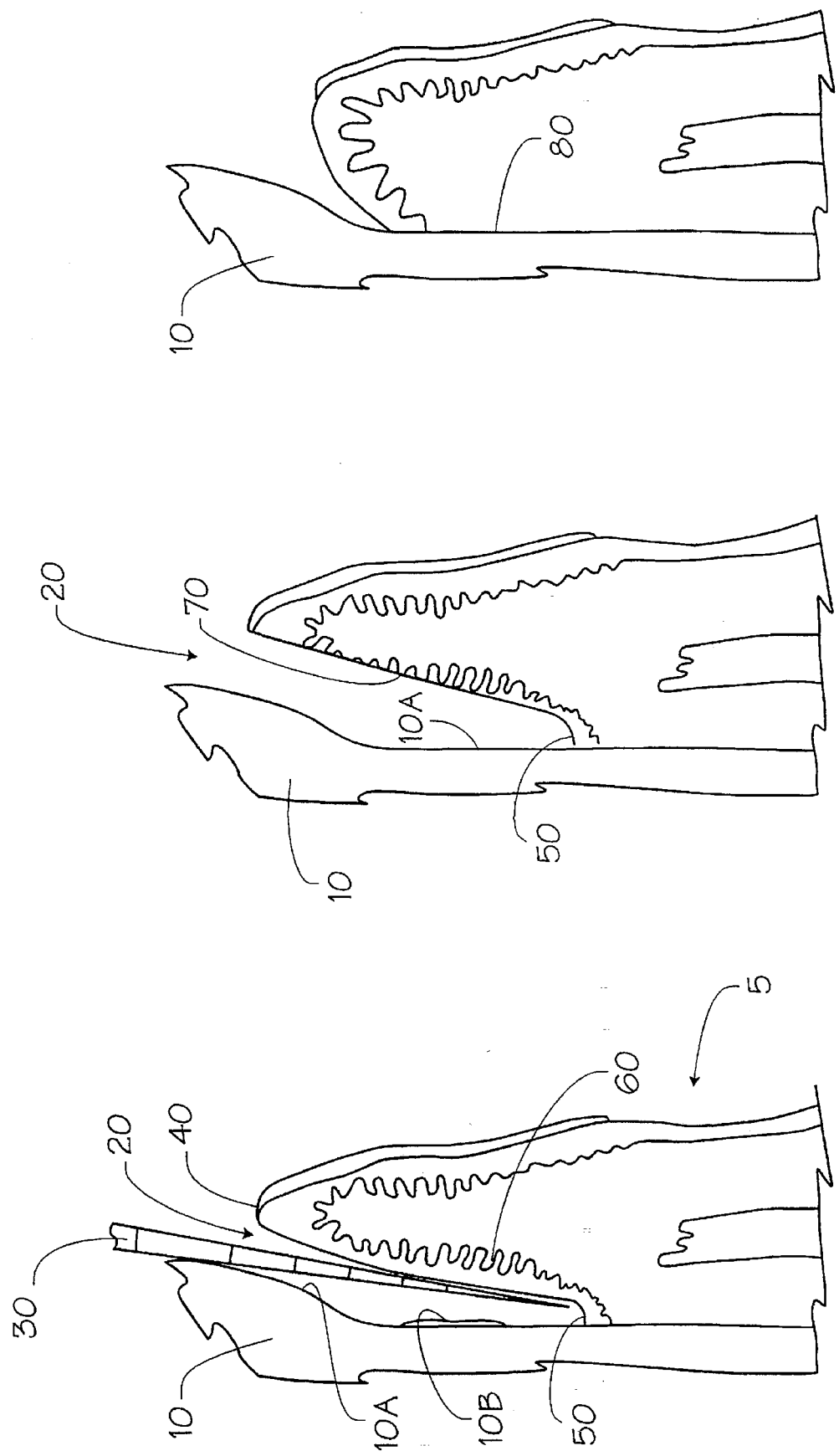

LASER EXCISIONAL NEW ATTACHMENT PROCEDURE

BACKGROUND OF THE INVENTION

1. Field of the Invention

This invention relates generally to surgical procedures, and more particularly to an improved surgical method for eliminating a condition of deep gingival pockets and the disease associated with this condition.

2. Description of Related Art

Periodontal diseases are caused by certain types of bacteria in plaque. These bacteria create toxins which irritate the gums and result in a break down of the attachment of the gum tissues to the teeth. Over time, these toxins can destroy gum tissues, and allowing the infection to progress, can result in bone loss. There are many forms of gingival and periodontal diseases, the most common types being gingivitis and adult periodontitis. Gingivitis is the earliest stage, and affects only the gum tissue. At this stage, the disease is still reversible. If not treated, however, it may lead to a more severe condition called periodontitis. The gums, bone and other structures that support the teeth become damaged. Teeth can become loose and may have to be removed. At this stage, the disease may require more complex treatment to prevent tooth loss. With healthy gingiva (gum tissue), the teeth are firmly anchored in place. Gingivitis develops as toxins in plaque irritate the gums, making them red, tender, swollen and likely to bleed easily. Periodontitis occurs when toxins destroy the tissues that anchor the in the bone. Gums become detached from the teeth, forming pockets that fill with more plaque. Tooth roots are exposed to plaque and become susceptible to decay and sensitive to cold and touch. Advanced periodontitis is present when the teeth lose more attachment because the supporting bone is destroyed. Unless treated, the affected tooth frequently become loose and may fall out. The method of treatment of periodontal diseases depends upon the type of disease and how far the condition has progressed. The first step usually a thorough cleaning which may include scaling to remove plaque and calculus deposits beneath the gum line. The tooth roots may also be planed to smooth the root surface so that the gingiva may heal next to the teeth. Surgery may be required when deeper pockets, usually over 4 to 6 mm, are found. It is difficult for the dentist or hygienist to thoroughly remove plaque and calculus from deep pockets. Patients can seldom keep them clean and free of plaque. Allowing pockets to remain may invite infection and bone destruction. When pockets are deep and bone has been destroyed, flap surgery may be necessary to provide access to the roots of the teeth in order to thoroughly remove calculus, plaque and any diseased tissue, and to recontour the bone to a more favorable architecture. In this technique, the gum is lifted away and is then sutured back into place or into a new position that will be easier to keep clean. The prior art teaches the use of surgical debridement of the root surface and the removal of granulation tissue following the resection of the soft tissue flap. Aesthetic modifications of this approach have been reported under the title of open flap curettage, reverse bevel flap surgery, Widman flap surgery and modifications of Widman flap surgery and apically positioned flap osseous surgery, guided tissue regeneration.

Relevant prior art publications include:

White, J. M. et al, Journal of Periodontology, 1994 July, 65(7):733–5 entitled; "Current status of lasers in soft tissue dental surgery".

Israel, M. et al, JOP, 1995 March, 66(3):197–204 entitled; "Predictable regeneration of tooth-supporting tissues.

Golub, L. M. et al, Journal of Clinical Periodontology, 1995 February, 22(2):100–9 entitled; "Doxycycline inhibits neutrophil (PMN) type matrix mealloproteinases in human adult periodontitis gingiva".

Israel, M. Practical Periodontics and Aesthetic Dentistry, 1994 August, 6(60–64) entitled; "Use of the CO2 laser in soft tissue and periodontal surgery".

Gold, S. I. et al, JOCP, 1994 July, 21(6):391–6 entitled; "Pulsed laser beam effects on gingiva".

The literature is rich with technique and apparatus using lasers in dental and other medical applications. We do not find a method for the removal of the deep gingival pocket, elimination of disease and reattachment of the gingiva to the tooth surface. The present invention fulfills these needs and provides further related advantages as described in the following summary.

SUMMARY OF THE INVENTION

The primary object of the present invention method is to treat gingivitis or gum disease. It is a further object of the present invention to eliminate gingival pockets by establishing a new connective tissue attachment to the tooth at, or near, the coronal level by producing a long junctional epithelium. The inflamed sulcular and pocket epithelium is excised without substantially removing any connective tissue. The procedure of the invention, as described and claimed, is indicated when there is a moderate-to-deep, as probed pocket depth of five mm or greater, as measured from the coronal to the muco-gingival junction, and when any of the following is present:

Bony defects visible and/or probable.

Infection in the gingival tissue

Mobility of the dentition.

Esthetic considerations.

The objects of the present invention are accomplished by excising the inner pocket epithelium around the entire tooth to a depth equal to an initial probe reading of the inner pocket, followed by an ultrasonic scaling of root surfaces and root planing and scaling of all cementum. The procedure further includes cleaning steps and a lasing of the pocket in preparation for tissue welding. The procedure is categorized as a Gingival Flap Procedure and limited or complete occlusal adjustment. Treatment time of 120 minutes is reasonable to perform two quadrants. Treatment is followed by a coronal polishing/prophylaxis and an occlusal equilibration follow-up and a post-op check of the area treated.

A topically placed anesthetic is used to anesthetize the area. Begin with 4% Prilocaine Plain, using a 30 gauge needle. This anesthetic is perceived by the patient as painless, due to its unique ability to anesthetize soft tissue without stinging. Inject the anesthetic very slowly into the area, allowing several minutes for the Prilocaine Plain to take effect. Continue using a 30 gauge needle, and follow this procedure with a suitable longer-acting anesthetic. However, an exception would be made if health reasons caused the anesthetic to be contraindicated. The area of concern usually involves two quadrants, or alternatively, one arch, either upper or lower. Anesthesia is routinely used in every procedure for the reasons set forth below:

a) aiding in accurate measurement of the full-depth of the diseased pocket;

b) to be aggressive in the root planing and scaling of all surfaces of the tooth;

c) allowing the patient to be as comfortable as possible during the treatment, thereby minimizing the patient's endogenous adrenaline production, and in turn achieve the optimal therapy results;

d) maximize the doctor's ability to concentrate on the procedure; and e) to optimize the use of ultrasonic probes at frequencies between one hertz and three hundred thousand hertz.

The pocket depths should then be recorded with a periodontal probe with six areas recorded around each tooth. This will allow a determination of the full depth of the diseased pocket. A laser, such as provided by Sunrise Corporation, their model number "d-lase 300", operating at a wavelength of between 400 and 12,000 nanometers is used to create the initial excisional trough at the marginal gingiva using between one and one hundred watts of fiber output power (measured at the distal end of the fiber), and frequencies between one hertz and three hundred megahertz. Additionally, the appropriate application of intermittent or simultaneous water spray should be used for tissue cooling. A contact laser fiber with a fiber diameter of between 100 μ (microns) and 1000 μ (microns) should be used, in an orientation along the long axis of the tooth, to create a gingival trough by excising the free gingival margin and the internal epithelial lining of the pocket, thus, exposing the root surface and removing all internal epithelial from the gingival pocket.

Appropriately cleaved contact laser fibers are used for the precise control of the laser energy, the physical placement of the laser energy, and the determination of the desired orientation of the laser to the tissue desired to be removed. Orientation along the long axis of the tool defines the direction of the laser fiber for the proper initial excision. The root surface is then opened by gingival troughing for viewing.

Excising the free gingival margin with the laser energy removes accretions and pathogens within the tissue of the free margin, which otherwise would not be removable. Additionally, this procedure provides hemostasis for better visualization, and further defines the tissue margins preceding mechanical instrumentation. The integrity of the mucosa is also preserved by releasing tissue tension around the tooth prior to mechanical manipulation, thereby dissecting the separation between the free gingival margin and the fibrous collagen matrix, which holds the gingiva in position. Maintenance of the crest of the gingival margin is aided in that the healing of the fibrous collagen matrix will maintain the gingival crest at, or better, than the presurgical level.

By use of the "hot-tip" effect (accumulated tissue proteins heated conductivity secondary to the passage of laser energy through the fiber), continue to excise the inner pocket epithelium around the entire tooth to the depth of the probed reading (Do Not attempt to break through the mucogingival junction.) This effect provides the selective removal of sulcular, pocket epithelium and granulation tissue without removing any substantial connective fibrous tissue and does so circumferentially, as long as the area is not allowed to become dry during surgery. As necessary, remove the excised tissue that accumulates on the tip of the laser fiber.

Next, ultrasonically scale all root surfaces to the depth of the pocket. The intent is to remove all foreign structures and substances from the pocket, thereby allowing adhesion of the lased soft tissue to the clean tooth surface. Next, carefully root plane and scale all cementum. This can be augmented by the use of the, well known, small "spoon like" bone files which clean the surface on the cementum exceptionally well.

Between one and one hundred watts of fiber output power and a frequency between one hertz and three hundred megahertz will then be used in the deep periodontal pockets for optimal bacterial destruction without causing bacterial injection into the periodontal tissues. This will minimize a soft tissue cellulitis. By using the laser fiber explore for remaining calculus and/or root roughness. These small fibers are very adept at detection of any surface irregularities. Continue or repeat, if necessary, any or all of the steps above, as needed, to achieve a smooth and clean root surface.

Again, the laser is used in the pocket to remove large areas of granulation tissue, disinfect tissue, assist in hemostasis, cauterize free nerve endings, seal lymphatics and prepare tissue for welding and desensitizing teeth. The area should be rinsed with water to remove any residue, calculus or blood clots; also, the laser may be used for touch-up if needed.

Elimination of all occlusal prematurities and interferences, centric working and balancing is done to allow healing of the tissue and bone regeneration. An occlusal splint is necessary when trauma induced periodontal disease is manifest, i.e., occlusal trauma in the presence of bacteria induced periodontal disease. Master impressions for a mandibular occlusal splint are taken. The splint is designed to provide anterior guidance, i.e., a "Tanner Splint", and is the appliance of choice. The splint will be delivered at the appointment that is scheduled one week after the postoperative appointment. At this time it will be adjusted accordingly for tooth stabilization.

All treatment sites are irrigated to the deepest depth of the periodontal pockets with a bactericidal solution consisting of a high tissue substantivity (e.g., chlorhexadine gluconate 0.12%). The irrigation aids the laser in the reduction of bacteria in the pocket and in removing debris.

Approximate the wound edges and, using the laser, control oozing as needed. Healing of the wound edges by secondary intention is imperative.

The tissues should be compressed with wet gauze for two to three minutes against the tooth from both a facial and lingual direction, permitting only a thin clot to form between the tissue and the tooth.

Medications should be prescribed for home use, and a review of post-operative care should be discussed with the patient. A post-operative appointment should be scheduled within seven to ten days. Perform a through occlusal equilibration follow-up.

This treatment should be continued periodically until bone development is complete. Appointments should continue for one full year.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention, a method for eliminating gingival pockets and for establishing a long junctional epithelium. In such drawings:

FIG. 1 is a section of a gingival tissue prior to the administration of the method of the invention;

FIG. 2 is a section of the same gingival tissue as in FIG. 1 showing the position of surgical tissue severing; and FIG. 3 is a section of the same gingival tissue as in FIG. 1 after completion of the method of the invention.

DETAILED DESCRIPTION OF THE PREFERRED EMBODIMENT

The above described drawing figures illustrate a method for treating gingival disease. An excisional new attachment procedure comprises a step-by-step approach. First, the gingival tissue 5 corresponding to a targeted tooth 10 is anesthetized. The depth of a pocket 20 in the gingival tissue is measured, preferably with a periodontal probe 30, taking at least six spaced apart measurements around the tooth 10. The pocket depth is defined as extending from the upper gingival margin 40 to the mucogingival junction 50. The interior epithelial lining 60 of the pocket 20 is then ablated and vaporized to the full depth of the pocket 20, preferably using a laser fiber having a preferred diameter of between 100 microns and 1000 microns, the fiber preferably held oriented with the axis of the tooth 10. This is completed and on all sides of the tooth 10. This step generates and prepares a new pocket tissue surface 70. Preferably not more than 100 watts of fiber output power is used, as measured at a distal end of the fiber, and a lasing frequency of not more than 300 megahertz is preferably applied. Preferably, water is sprayed into the pocket 20 for cooling during the ablating and vaporizing step.

Next, the surface of the tooth 10A is cleaned of all foreign matter 10B, again, to the depth of the pocket 20 on all sides of the tooth 10. Next, the pocket 10 is lased to remove granulation tissue, and to disinfect, assist in hemostatis, cauterize free nerve endings, and seal lymphatics, of the pocket tissue surface. Lasing also prepares the pocket tissue surface 70 for welding, and also desensitizes the tooth. All debris is then rinsed from the pocket 20. This is followed by an irrigation of the pocket 20 with a bactericidal solution.

Next, occlusal interferences are eliminated. The new pocket tissue surface 70 is lased to adapt it for tissue welding. The pocket tissue surface 70 is approximated with the tooth surface 10A preferably using wet gauze to hold the pocket tissue surface 70 in contact with the tooth surface 10A, preferably for, from 2 to 3 minutes allowing a thin clot 80 to form between the pocket tissue surface 70 and the tooth surface 10A so as to advance and assure adhesion of these tissues. Finally, the bodies natural immune system is enhanced by prescribed medications for outpatient use in preventing infection. This important step is necessary in order to protect against infection and reduce inflammation. The procedure preferably includes the further step of providing at least one subsequent occlusal equilibration examination.

A recapitulation of the above description with further details follows:

The area of concern, usually two quadrants is anesthetized. The procedure is applied independently to each tooth involved. Pocket depth is measured and recorded with a perio probe to determine, the full depth of the diseased pocket. A contact laser fiber is oriented along the long axis of the tooth, and is used to create a gingival trough by excising the free gingival margin and the internal epithelial lining of the pocket, thereby exposing the root surface. Appropriately cleaved contact laser fibers provide precise control of the laser energy, the physical placement of the laser energy, and the determination of the desired physical orientation of the laser to the tissue to be removed. Gingival troughing is used to open the root surface for visualization. Excision of the free gingival margin removes accretions and pathogens within the tissue of the free margin which are otherwise unremovable, and provides hemostasis for better visualization. This step also defines the tissue margins preceding mechanical instrumentation, and preserves the integrity of the mucosa by releasing tissue tension. It also dissects-out the separation between the free gingival margin and the fibrous collagen matrix which holds the gingiva in position. This aids in the maintenance of the crest of the gingival margin. Using the "hot-tip" effect, further excise of the inner pocket epithelium around the entire tooth is completed, to the depth of the probe readings. No attempt is made to break through the muco-gingival junction. The "hot-tip" effect (accumulated tissue proteins heated conductivity secondary to the passage of laser energy through the fiber) provides the selective removal of sulcular and pocket epithelium and granulation tissue without removing substantially any connective fibrous tissue, and does so circumferentially. As necessary, the excised tissue that accumulates on the tip of the laser fiber is removed. Ultrasonic scaling of all root surfaces to the depth of pocket is completed. The intent is to remove all foreign structures and substance from the pocket to allow adhesion of the soft tissue to the clean tooth surface. Careful root planing and scaling of all cementurn is completed. This can be augmented by the use of small, spoon-like bone files, which are highly effective in cleaning the surface of the cementurn. Using the laser fiber explore for remaining calculus and/or root roughness. These small fibers are very adept at detection of any surface irregularities. Lasing of the pocket to remove large areas of granulation tissue, disinfect tissue, assist in hemostasis, cauterize free nerve endings, seal lymphatics, prepare tissue for welding and desensitize those teeth that are sensitive is accomplished. The areas are rinsed with water to remove any residue, calculus and blood clots. Elimination of all occlusal interferences, centric, working and balancing is completed. For best results this step is imperative since it allows the tissue to heal and the bone to regenerate. The laser modifies the tissue to allow new attachment to take place but if the trauma of malocclusion continues the tissue cannot withstand and begins to brake down immediately. All treatment sites are irrigated to the deepest depth of the periodontal pockets with a bactericidal solution consisting of a high tissue substantivity (e.g., chlorhexadine gluconate 0.12%). The irrigation aids the laser in the reduction of bacteria in the pocket and in removing debris. This aids the laser in reduction of bacteria in the pocket. Approximation of the wound edges is completed. Lasing is further accomplished to control oozing as needed. Healing of the wound edges by secondary intention is imperative. The tissue is compressed with a wet gauze for 2 to 3 minutes against the tooth from both a facial and lingual direction in order to permit only a thin clot to form between the tissue and the tooth.

Post procedural steps include prescribing medications for home use and reviewing post-op care with the patient. Master impressions for a mandibular occlusal splint are taken. The splint is designed to provide anterior guidance, i.e., a "Tanner Splint", and is the appliance of choice. This will be delivered at the post-op appointment and adjusted as needed for tooth/teeth stabilization. A thorough occlusal equilibration follow-up examination is required. This treatment should continue periodically until bone development is complete. Pocket-depth readings at 60, 120 and 180 days during continuing care appointments are desirable.

While the invention method has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An excisional new attachment procedure comprising the steps of:

a) anesthetizing a gingival tissue corresponding to a targeted tooth, of a patient the tooth having a tooth surface;

b) measuring a depth of a pocket in the gingival tissue, from an upper gingival margin to a mucogingival junction;

c) ablating and vaporizing an interior epithelial lining of the pocket, to the depth of the pocket on all sides of the tooth to prepare a new pocket tissue surface;

d) cleaning the tooth surface of all foreign matter, to the depth of the pocket on all sides of the tooth;

e) lasing the pocket to remove granulation tissue, and to: disinfect, assist in hemostatis, cauterize free nerve endings, and seal lymphatics, of the pocket tissue surface, and to prepare the pocket tissue surface for welding, and to desensitize the tooth;

f) rinsing the pocket to remove debris; and g) irrigating the pocket with a bactericidal solution;

h) eliminating occlusal interferences;

i) lasing the pocket tissue surface to adapt the pocket tissue surface for tissue welding;

j) approximating the pocket tissue surface with the tooth surface; and k) maintaining the pocket tissue surface in contact with the tooth surface to advance adhesion.

2. The method of claim 1 wherein the ablating and vaporizing, and the lasing is completed with a laser fiber held oriented with the axis of the tooth.

3. The method of claim 1 wherein the depth measuring is completed with a periodontal probe taking at least six spaced apart measurements around the tooth.

4. The method of claim 1 further including the step of providing a laser, wherein the ablating and vaporizing is completed with not more than 100 watts of output power from the laser, as measured at a distal end of a laser fiber of the laser, and with a lasing frequency of not more than 300 megahertz.

5. The method of claim 4 further including the step of spraying water onto the pocket tissue surface for cooling the pocket tissue surface during step (c).

6. The method of claim 4 wherein the laser fiber is of a diameter of between approximately 100 microns and 1000 microns.

7. The method of claim 1 wherein step (k) further comprising using wet gauze to hold the pocket tissue surface in contact with the tooth surface for, from 2 to 3 minutes allowing a thin clot to form between the pocket tissue surface and the tooth surface.

8. The method of claim 1 further including the step of prescribing medications for outpatient use in preventing infection.

9. The method of claim 1 further including the step of providing at least one subsequent occlusal equilibration examination.

10. The method of claim 1, further comprising the step of enhancing the patient's natural immune system to protect against infection and reduce inflammation.

* * * * *